(12) United States Patent
Vermeiden et al.

(10) Patent No.: US 6,551,554 B1
(45) Date of Patent: Apr. 22, 2003

(54) COUNTING COMPARTMENT FOR BIOLOGICAL INVESTIGATIONS AND A METHOD FOR MANUFACTURING SUCH A COUNTING COMPARTMENT

(75) Inventors: Jan P. W. Vermeiden, Vreeland (NL); Leonardus A. J. M. Van De Rotten, Mijdrecht (NL)

(73) Assignees: Leja Products B.V. (NL); Alfons P.A.G. De Kock (NL)

( * ) Notice: Subject to any disclaimer, the term of this patent is extended or adjusted under 35 U.S.C. 154(b) by 0 days.

(21) Appl. No.: 08/894,455

(22) PCT Filed: Feb. 13, 1996

(86) PCT No.: PCT/NL96/00068

§ 371 (c)(1),
(2), (4) Date: Jan. 30, 2001

(87) PCT Pub. No.: WO96/25682

PCT Pub. Date: Aug. 22, 1996

(30) Foreign Application Priority Data

Feb. 15, 1995  (NL) .............................................. 9500281

(51) Int. Cl.$^7$ .............................................. G01N 21/03
(52) U.S. Cl. ..................... 422/58; 422/57; 422/102; 422/939; 422/940; 435/287.9; 435/288.3; 356/244; 356/246
(58) Field of Search .............................. 422/55, 57, 58, 422/99, 102, 939, 940; 435/287.9, 288.3; 356/244, 246

(56) References Cited

U.S. PATENT DOCUMENTS

| 3,198,064 A | * | 8/1965 | Moore ......................... 206/205 |
|---|---|---|---|
| 3,447,863 A | | 6/1969 | Patterson |
| 3,742,600 A | * | 7/1973 | Lowell ........................ 264/500 |
| 4,022,521 A | * | 5/1977 | Hall et al. ................... 356/244 |
| 4,171,866 A | * | 10/1979 | Tolles .......................... 356/244 |
| 4,447,140 A | * | 5/1984 | Campbell et al. ........... 359/396 |
| 4,689,307 A | | 8/1987 | Schwartz |
| 4,790,640 A | * | 12/1988 | Nason .......................... 156/99 |
| 4,911,782 A | * | 3/1990 | Brown ......................... 216/33 |
| 5,039,487 A | * | 8/1991 | Smith ........................... 422/56 |
| 5,200,152 A | * | 4/1993 | Brown ........................ 356/244 |

FOREIGN PATENT DOCUMENTS

| EP | 0321889 | 6/1989 |
|---|---|---|
| WO | 9120009 | 12/1991 |

* cited by examiner

Primary Examiner—Maureen M. Wallenhorst
(74) Attorney, Agent, or Firm—Brooks & Kushman P.C.

(57) ABSTRACT

Counting compartment having an inlet and an outlet, and including a bottom plate and a top plate which are held at a distance from each other by material particles which have the same size and are situated at a distance from one another. The particles are surrounded by and embedded in a solid connecting layer formed by an adhesive. The connecting layer extends all around and up to the free end of the outlet of the counting compartment. A fluent mixture of an adhesive mixed with electrostatically charged particles is used to form the counting compartment, the largest size of the material particles determining the depth of the counting compartment. The counting compartment is particularly suitable for counting cells in biological materials such as sperm and blood samples.

27 Claims, 2 Drawing Sheets

COUNTING COMPARTMENT FOR BIOLOGICAL INVESTIGATIONS AND A METHOD FOR MANUFACTURING SUCH A COUNTING COMPARTMENT

The invention relates to a counting compartment for accommodating a sample of biological material consisting of microscopic particles in a liquid medium for the quantitative microscopic examination of this material.

When examining body fluids, it is often desirable to study samples of such biological material under the microscope over a certain time. When examining sperm, for example, the aim is to establish how many spermatozoa are present in the sample and also how motile they are.

To carry out this investigation, a sample of a certain thickness is to be subjected to microscopic examination in a counting compartment, using a grid built into the eyelens of the microscope. Such a grid may be divided into a hundred squares, and the number of spermatozoa in each of a representative number of squares can be counted by the investigator in order to determine the total number of spermatozoa in the whole grid area. Such a grid may also be provided in the counting compartment. The number of spermatozoa in a square can be e.g. about one hundred to twohundred.

From U.S. Pat. Nos. 4,911,782 and 5,200,152 a method is known for conducting such determinations with the aid of a counting compartment formed by two transparent plates joined together by a connecting layer composed of a cured plastic.

However, the manufacture of such a counting compartment is complicated and expensive, because it involves the use of a photo-resist method for applying a plastic as the desired boundary of the compartment.

The aim of the present invention is to provide a counting compartment and a manufacturing method for it, which do not have this shortcoming and do not involve the use of the photo-resist method.

This aim is achieved according to the present invention by a counting compartment of the type indicated above, which is characterized in that the connecting layer contains material particles which are separate from one another and have a size which determines the depth of the counting compartment, which material particles are essentially in contact with the two plates.

The counting compartment can easily be constructed by using material particles which have a size which determines the depth of the counting compartment; furthermore, counting compartments with depths suitable for different biological materials can be produced by using material particles of appropriate dimensions.

The fact is that the examination of a sperm sample calls for a counting compartment with a depth of 12–20 microns, while the examination of blood cells needs a counting compartment with a depth of only 8–12 microns. Counting compartments with the required depth can be made by choosing material particles of the right size from amongst material particles measuring between 6 and 40 microns.

The particles which determine the depth of the counting compartment lie at a regular distance from one another in order to ensure a uniform depth for the counting compartment over its entire surface. Preferably, these particles, when their masses are equal, are at equal distances from one another. Furthermore, and preferably, these particles are substantially completely surrounded by the solid material of the connecting layer, formed from a fluent material.

To prevent clotting of these material particles, the particulate material chosen is preferably a non-magnetic, electrically highly resistant substance and, more preferably, aluminium oxide, but other materials and even plastic particles can also be used.

To prevent escaping, by capillary action, and evaporation of liquid from the sample of biological material consisting of microscopic particles in the counting compartment, the solid material of the connecting layer extends all round and up to the free end of the outlet of the compartment. This minimizes evaporation, so that no streaming occurs in the sample housed in the counting compartment.

The top and bottom plate are preferably both made of a material which transmits UV and/or visible light, preferably glass, and the top plate should be selected to be as thin as possible in order to facilitate the examination by means of a microscope.

The invention also relates to a method for the manufacturing of a counting compartment to accommodate a sample of biological material consisting of microscopic particles in a liquid medium for the quantitative microscopic examination of this material, which counting compartment comprises two transparent plates held at a fixed distance from each other and joined together by a connecting layer, and at least one counting compartment situated between the plates, bounded by the connecting layer and fitted with an inlet and an outlet. According to the invention, this method is characterized in that a fluent mixture of mutually repelling material particles and a liquid adhesive is applied to one of the plates, the other plate is placed on this fluent mixture, and pressure is exerted thereon until the two plates are essentially in contact with the largest material particles in the fluent material, which largest material particles determine the depth of the counting compartment.

It will be obvious that by using the above liquid mixture, one can easily apply this mixture to one of the plates, and the other plate can then be pressed on to this liquid material until the two plates are in contact with the largest particles present in the fluent mixture.

The mutually repelling material particles preferably carry an electrostatic charge and consist of a non-magnetic, electrically strongly insulating, material and are then charged electrostatically.

By using particles carrying an electrostatic charge, the particles will always lie at the same distance from one another, this distance depending on the size of the particle and on the charge.

A counting compartment according to the invention can be used to carry out biological determinations on samples of sperm, of blood and of malignant tissue, such as cancer.

From U.S. Pat. No. 4,689,307 it is known to provide microbeads as spacers between microscope slide and coverslip around a sample for microscopic investigation. They can be added in advance to an aqueous liquid.

From EP-A 0 321 889 it is known to provide microbeads onto a microscope slide by fixing them in advance in a solid residue of dried liquid adhesive. This adhesive is soluble in the sample to be examined.

Neither one of these publications discloses the use of microparticles in a solid connecting layer for the formation of a counting compartment. Furthermore, there is no indication for the manner in which microspheres or other material particles which determine the spacing can be added without clotting to a viscous mass which, after curing, will not dissolve into the sample under examination.

The invention will be explained in more detail below with reference to the drawing of an illustrative embodiment, in which.

Figure 1:
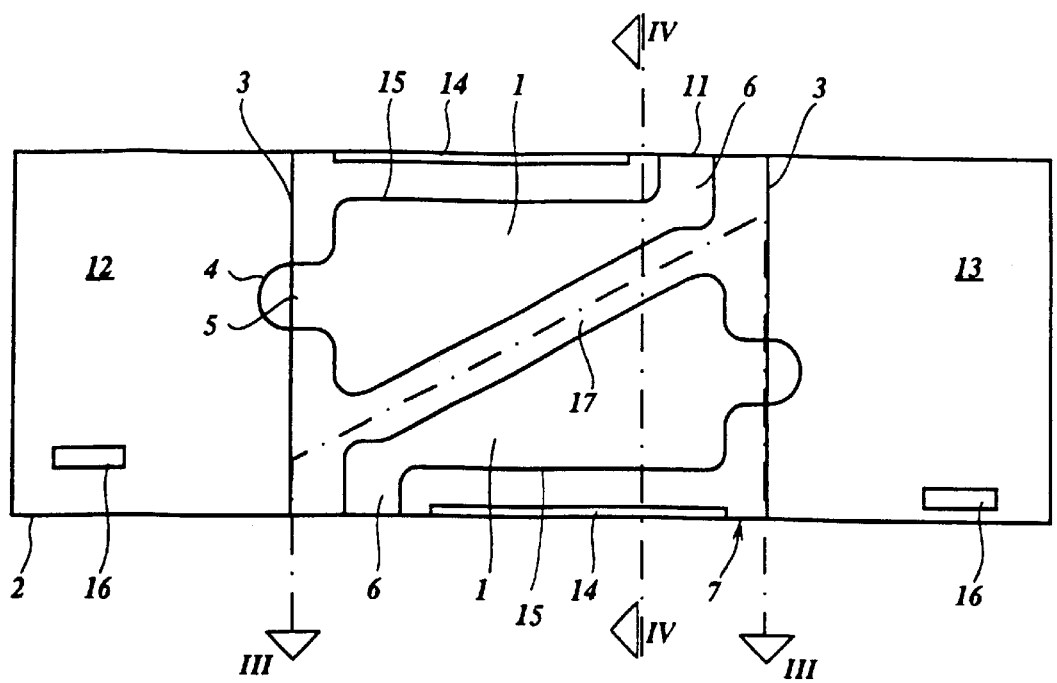
FIG. 1 shows a plan view of a counting compartment according to the invention.
Figure 4:
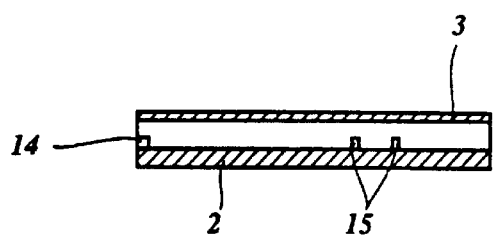
FIG. 4 shows a cross-section taken along line IV—IV in FIG. 1.

The counting compartment 1 is formed by taking a flat glass bottom plate 2 and printing on one of its faces, a pattern which comprises strips 12 and 13 at both ends of the plate, and two strips 14 along each of the edges of the plate. Furthermore, preferably on the face of bottomplate 2 oriented towards top plate 3 to be provided later, a strip 15 is printed, bounding the periphery of a counting compartment, by which the examination with such counting compartment is made easier. The height of strips 12, 13, 14 and 15 is about 4–6 microns.

The inlet 5 of the compartment is formed by a space 4 in the end strip 12 or 13 adjoining the boundary strip 15.

Information 16 relating to the contents of the counting compartment can be given on the strips 12 and 13.

These strips 12, 13, 14 and 15 are made by means of a doctor blade using ink or dabber printing technique. The ink used is allowed to dry in air or, depending on the type of ink used, is made to set under UV light. The ink used should, as a matter of course, adhere to the glas, and it may not be soluble in bodily fluids.

Figure 2:
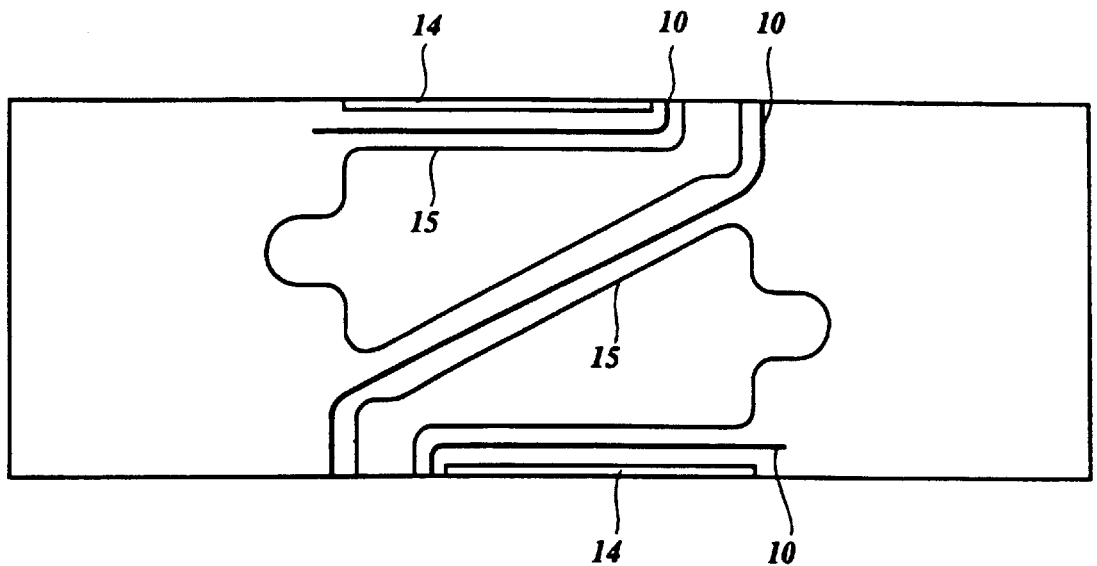
FIG. 2 shows a plan view of the bottom plate of the counting compartment after printing and the application of a fluent mixture of adhesive and material particles thereto.

A fluent mixture consisting of a polyester adhesive 9 (FIG. 3) and aluminium oxide particles 8, which have previously been electrostatically charged and which are therefore mutually repellent, is then applied to the bottom plate 2, in form of strips 10 (FIG. 2). The material particles 8 having the largest dimensions will determine the depth of the counting compartment 1.

A suitable maximum size of the particles can be selected beforehand by first screening the material, which also permits the depth of the counting compartment to be regulated.

Figure 3:
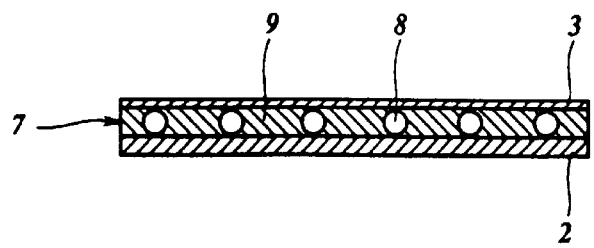
FIG. 3 shows a cross-section taken along line III—III in FIG. 1.

When strips 10 of said fluent mixture have been applied, a top plate 3 is pressed on until the bottom surface thereof contacts the largest of the material particles 8 present in the mixture (see FIG. 3). At the same time, the fluid mixture of strips 10 is spread to form a connecting layer 7, which extends at least all round and up to the free end 11 of the outlet 6 of the compartment. The connecting layer 7 is then allowed to solidify so as to obtain a solid connecting mass.

Evaporation of a sample introduced into the counting compartment is minimized by ensuring that the solid connecting layer 7 extends all round and up to the free end 11 of the outlet of the compartment. This eliminates streaming in the sample to be examined under a microscope. It is important for the connecting layer to fill the space between bottom plate and top plate at least up to the edges of the plates, in order to oppose lateral spreading of the sample situated close to the outlet 6 by capillary effect.

Expediently, the bottom plate 2 is a standard microscope slide measuring 7.5×2.5 cm, and the top plate is a standard cover slip measuring 3.2×2.5 cm.

As can be seen from FIG. 1, two counting compartments 1 have been formed on the bottom plate. The solid connecting mass 17 separating the two counting compartments forms an adequate barrier which prevents the sample material from moving from one counting compartment to the other. For counting spermatozoa preferably elongated compartments are used.

Counting compartments with a depth of 12, 20, 30 and 40 microns can be formed by using aluminium oxide particles 8 whose largest dimensions are 6 or 8, 10, 18, 28 and 38 microns, respectively. When counting spermatozoa 8' in sperm, it is expedient to set the counting compartment at a depth obtained by using particles, the largest of which measure 18 microns, with which the compartment depth becomes 20 microns. In addition to these particles with the required maximum dimensions, the material particles 8 can of course also contain smaller particles 8, but they do not determine the distance between the bottom plate 2 and the top plate 3.

Figure 5:
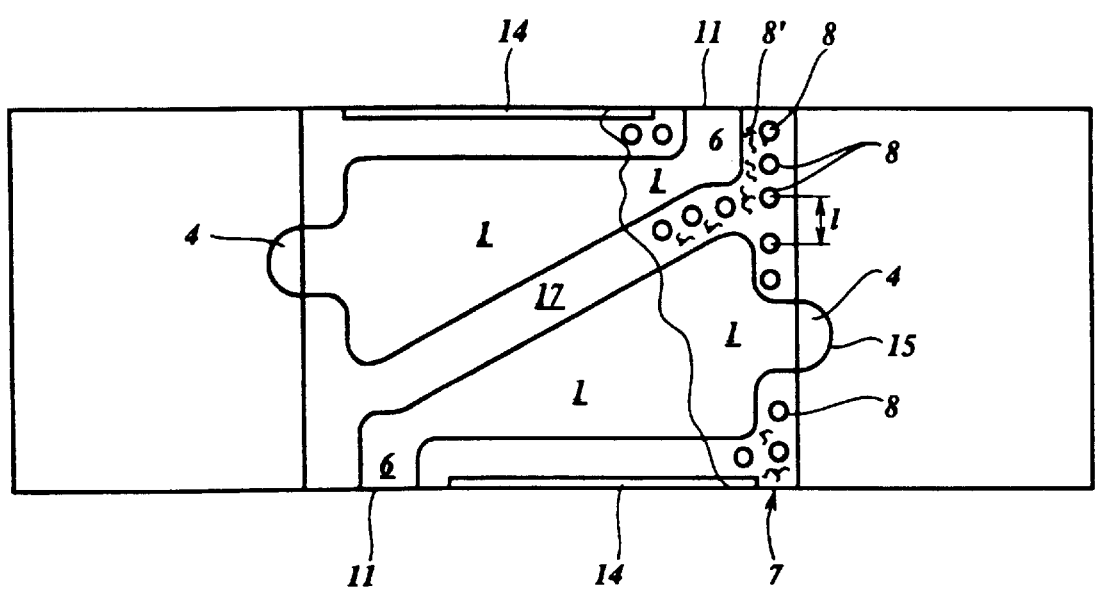
FIG. 5 shows a view according to FIG. 1 but with part of the top plate removed.

Owing to the electrostatic charge applied to the aluminium oxide particles 8 which are mixed with the polyester adhesive 9, the largest particles in the finished counting compartment 1 will all be situated at the same distance from one another (l, see FIG. 5) on account of the repulsion between these particles.

Although aluminium oxide particles 8 are mentioned above, plastic particles can also be used, provided that they are not soluble in, attacked by or deformed by the adhesive. Glass beads can also be used, although they are somewhat more difficult to charge on account of their hycroscopic property. Another suitable material for example, is magnesium oxide.

In addition to the largest particles 8, the material can of course also contain a number of smaller aluminium oxide particles, since a fraction with the largest particles as the upper size limit is screened out of the starting material.

Electrostatically, preferably positively charging the particles is preferably carried out by making the particles move through an electrostatic field. After that, the particles are collected in a glass container, in which the adhesive is added, the combination being stirred until the particles are divided evenly in the adhesive. As a result of the charge, no clots will form but the particles will come to lie at regular distances, determined by mass and charge.

The amount of material particles 8 added to the adhesive is suitably less than 10% and preferably at most 3%. Amounts of more than 3% do not give any further improvement.

The polyester adhesive 9 can be replaced by a silicone adhesive, a metacrylic resin or other synthetic resin. In any case the requirement is that the material must not be soluble in bodily liquids. Preferably also adhesive 9 is of a type which is UV-curing.

What is claimed is:

1. A counting compartment for accommodating a biological sample for microscopic examination thereof, the counting compartment comprising:

spaced top and bottom plates; and a connecting layer disposed between and joining the plates, to form a boundary which defines an unoccupied area of the counting compartment for placement of the biological sample, the connecting layer including spaced material particles therein which are substantially in contact with the plates along the boundary such that the size of the largest material particles determines the depth of the counting compartment, wherein the connecting layer is insoluble in the biological sample.

2. The counting compartment according to claim 1, wherein the boundary formed by the connecting layer include an inlet and an outlet.

3. The counting compartment according to claim 1, wherein the material particles lie at substantially equal distances from one another.

4. The counting compartment according to claim 1, wherein the material particles are electrostatically charged.

5. The counting compartment according to claim 1, wherein the material particles comprise a non-magnetic, electrically insulating material.

6. The counting compartment according to claim 1, wherein the material particles comprise aluminum oxide.

7. The counting compartment according to claim 1, wherein the material particles comprise a plastic material.

8. The counting compartment according to claim 1, wherein the material particles comprise glass.

9. The counting compartment according to claim 1, wherein the connecting layer further includes a fluent material mixed with and surrounding the material particles.

10. The counting compartment according to claim 9, wherein the fluent material comprises an adhesive.

11. The counting compartment according to claim 10, wherein the adhesive is selected from the group consisting of a polyester adhesive, a silicone adhesive, and a synthetic resin.

12. The counting compartment according to claim 10, wherein the adhesive is UV-curing.

13. The counting compartment according to claim 1, wherein the plates are transparent.

14. The counting compartment according to claim 1, further comprising strips provided on one of the plates which guide the formation of the boundary, wherein the height of the strips is less than the diameter of the largest material particles.

15. The counting compartment according to claim 1, wherein the material particles comprise less than about 10% of the volume of the connecting layer.

16. The counting compartment according to claim 1, wherein the material particle comprise about 3% of the volume of the connecting layer.

17. A method for manufacturing a counting compartment for accommodating a biological sample for microscopic examination thereof, the method comprising:

providing spaced top and bottom plates;

applying a connecting layer to one of the plates which forms a boundary that defines an unoccupied area of the counting compartment for placement of the biological sample, wherein the connecting layer is insoluble in the biological sample and includes spaced material particles therein; and joining the plates with the connecting layer disposed therebetween such that the material particles are substantially in contact with the plates along the boundary and the size of the largest material particles determines the depth of the counting compartment.

18. The method according to claim 17, wherein applying the connecting layer to form the boundary includes providing an inlet and an outlet to the counting compartment.

19. The method according to claim 17, wherein the material particles lie at substantially equal distances from one another in the connecting layer.

20. The method according to claim 17, wherein the material particles are electrostatically charged in the connecting layer.

21. The method according to claim 17, wherein the connecting layer includes a fluent material mixed with and surrounding the material particles.

22. The method according to claim 21, wherein the fluent material includes an adhesive.

23. The method according to clam 17, wherein providing spaced top and bottom plates includes providing transparent plates.

24. The method according to claim 17, further comprising applying strips on at least one of the plates which guide the formation of the boundary, wherein the height of the strips is less than the diameter of the largest material particles.

25. The method according to claim 17, wherein the material particles in the connecting layer comprise less than about 10% of the volume of the connecting layer.

26. The method according to claim 17, wherein the material particles in the connecting layer comprise about 3% of the volume of the connecting layer.

27. The method according to claim 17, further comprising screening the material particles based on their size prior to inclusion in the connecting layer.

* * * * *